United States Patent [19]

Hollenberg et al.

[11] Patent Number: 4,859,596
[45] Date of Patent: Aug. 22, 1989

[54] CLONING SYSTEM FOR KLUYVEROMYCES SPECIES

[75] Inventors: Cornelis P. Hollenberg; Sunil Das, both of Dusseldorf, Fed. Rep. of Germany; Albert De Leeuw, Pijnacker; Johannes A. van den Berg, Reeuwijk, both of Netherlands

[73] Assignee: Gist-Brocades N.V., MA Delft, Netherlands

[21] Appl. No.: 572,414

[22] Filed: Jan. 19, 1984

[30] Foreign Application Priority Data

May 19, 1982 [NL] Netherlands ................ 8202091
May 19, 1983 [WO] PCT Int'l Appl. ... PCT/EP83/00128

[51] Int. Cl.$^4$ ................ C12N 15/00; C12N 5/00; C12P 21/00; C07H 15/12
[52] U.S. Cl. ................ 435/172.3; 435/68; 435/91; 435/255; 435/317.1; 435/320; 935/28; 935/37; 935/56; 536/27
[58] Field of Search ............ 435/255, 226, 172.3, 435/68, 69, 70

[56] References Cited

U.S. PATENT DOCUMENTS

| | | | |
|---|---|---|---|
| 4,387,162 | 6/1983 | Aigle et al. | 435/255 |
| 4,418,150 | 10/1983 | Gunge . | |
| 4,657,857 | 7/1987 | Edins et al. | 435/68 |

FOREIGN PATENT DOCUMENTS

| | | |
|---|---|---|
| 81303167.1 | 7/1981 | European Pat. Off. . |
| 82100124.5 | 1/1982 | European Pat. Off. . |
| 82300949.3 | 2/1982 | European Pat. Off. . |
| 8202091 | 5/1982 | European Pat. Off. . |
| 82304460.7 | 8/1982 | European Pat. Off. . |
| 2094341A | 3/1982 | United Kingdom . |

OTHER PUBLICATIONS

Struhl et al. (1979), PNAS, 76: 1035–39.
Ito, H. et al. (1983), J. Bact, 153:163–168.
Hinnen, A. et al. (1978), PNAS, 75:1929–1933.
Hollenberg, C. (1982), In Curr. Topics. Micro and Immunol, 96:119–144.
Dickson, R. (1980), Gene, 10:347–356.
Stinchcomb, D. et al., 1980, PNAS, 77:4559–4563.
Beach, D. and P. Nurse, 1981, Nature, 290:140–142.
Hitzeman, R. et al., 1981, Nature, 293:717–722.
Roth et al., Mol. Cell. Biol., 3(11):1898 (1983).
Struhl et al., Nature, 305:391 (1983).
Gunge and Sakaguchi, J. Bacteriol: 147(1):155–160 (1981).
Hsiao and Carbon, Gene 15:157–166 (1981).
Patent Abstracts of Japan, vol. 5, No. 98 (C-60) (770), 25th Jun. 1981, JP-A-56 39099 (Mitsubishi Kasei Kogyo K.K.), 14-04-1981.

*Primary Examiner*—Thomas G. Wiseman
*Assistant Examiner*—Stephanie Seidman
*Attorney, Agent, or Firm*—Bertram I. Rowland

[57] ABSTRACT

A new cloning system is described capable of expressing genetic material derived from recombinant DNA material, which comprises a yeast of the genus Kluyveromyces as a host. Suitable vectors are e.g. vectors containing autonomously replicating sequences (ARS) and vectors containing homologous Kluyveromyces DNA acting as a site for recombination with the host chromosome. New and preferred vectors are those containing ARS sequences originating from Kluyveromyces (KARS vectors). The genetically engineered new strains of Kluyveromyces produce, inter alia, lactase and chymosin.

30 Claims, 12 Drawing Sheets

Figure 1
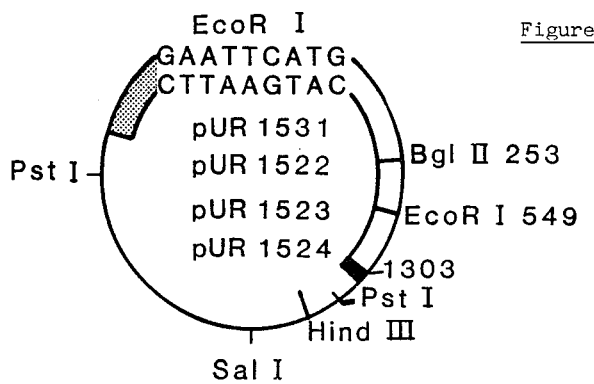
1. Partial EcoR I digestion (in the presence of ethidium bromide)
2. Sal I digestion
3. Purify EcoR I-Sal I fragments (1900-2150 bp) from agarose gel
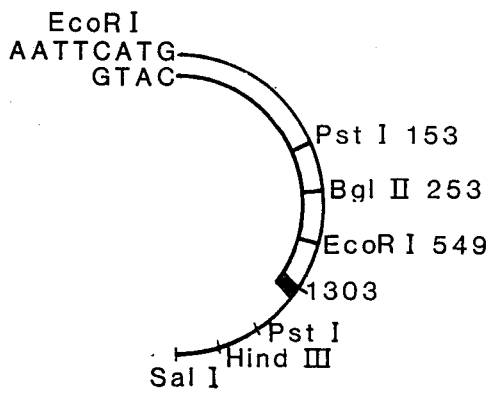
1) Fill-in cohesive ends with DNA polymerase (Klenow-fragment), 4 dNTP's
2) Add Sal I - linker (CGTCGACG / GCAGCTGC) with T4 DNA ligase, ATP
3) Hind III digestion
4) Sal I digestion
5) Purify Sal I - Hind III fragments from agarose gel
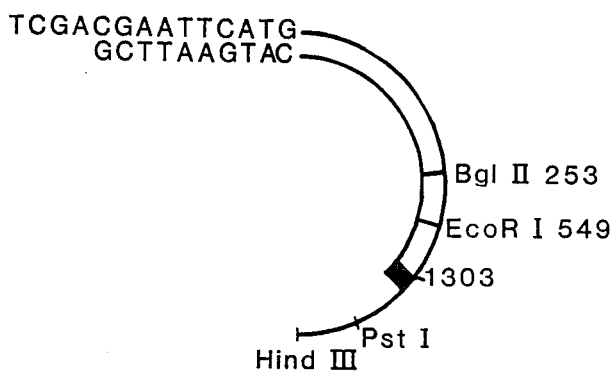
Fragments A, B, C, D

Figure 5

```
       -840       -830       -820       -810       -800       -790
   GAATTCCTCA GTTTCAAGAT CTTTTAATGT CCAAAACCAT TTGAGCCGAT CTAAATACTT
       -780       -770       -760       -750       -740       -730
   CTGTGTTTTC ATTAATTTAT AAATTGTACT CTTTTAAGAC ATGGAAAGTA CCAACATCGG
       -720       -710       -700       -690       -680       -670
   TTGAAACAGT TTTTCATTTA CATATGGTTT ATTGGTTTTT CCAGTGAATG ATTATTTGTC
       -660       -650       -640       -630       -620       -610
   GTTACCCTTT CGTAAAACTT CAAACACGTT TTTAAGTATT GTTAGTTGC TCTTTCGACA
       -600       -590       -580       -570       -560       -550
   TATATGATTA TCCCTGCGCG GCTAAAGTTA AAGATGCAAA AAACAGAAGA CAACTGAAGT
       -540       -530       -520       -510       -500       -490
   TAATTTACGT CAATTAAGTT TTCCAGGGTA ATGATGTTTT GGGCTTCCAC TAATTCAATA
       -480       -470       -460       -450       -440       -430
   AGTATGTCAT GAAATACGTT GTGAAGAGCA TCCAGAAATA ATGAAAAGAA ACAACGAAAC
       -420       -410       -400       -390       -380       -370
   TGGGTCGGCC TGTTGTTTCT TTTCTTTACC ACGTGATCTG CGGCATTTAC AGGAAGTCGC
       -360       -350       -340       -330       -320       -310
   GCGTTTTGCG CAGTTGTTGC AACGCAGCTA CGGCTAACAA AGCCTAGTGG AACTCGACTG
       -300       -290       -280       -270       -260       -250
   ATGTGTTAGG GCCTAAAACT GGTGGTGACA GCTGAAGTGA ACTATTCAAT CCAATCATGT
       -240       -230       -220       -210       -200       -190
   CATGGCTGTC ACAAAGACCT TGCGGACCGC ACGTACGAAC ACATACGTAT GCTAATATGT
       -180       -170       -160       -150       -140       -130
   GTTTTGATAG TACCCAGTGA TCGCAGACCT GCAATTTTTT TGTAGGTTTG GAAGAATATA
       -120       -110       -100        -90        -80        -70
   TAAAGGTTGC ACTCATTCAA GATAGTTTTT TTCTTGTGTG TCTATTCATT TTATTATTGT
        -60        -50        -40        -30        -20        -10
   TTGTTTAAAT GTTAAAAAAA CCAAGAACTT AGTTTCAAAT TAAATTCATC ACACAAACAA
         -1
   ACAAAACAAA ATG
```

Figure 6

```
              7         17         27         37         47         57
         TAAATTTAAC TCCTTAAGGT TACTTTAATG ATTTAGTTTT TATTATTAAT AATTCATGCT
             67         77         87         97        107        117
         CATGACATCT CATATACACG TTTATAAAAC TTAAATAGAT TGAAAATGTA TTAAAGATTC
            127        137        147        157        167        177
         CTCAGGGATT CGATTTTTTT GGAAGTTTTT GTTTTTTTTT CCTTGAGATG CTGTAGTATT
            187        197        207        217        227        237
         TGGGAACAAT TATACAATCG AAAGATATAT GCTTACATTC GACCGTTTTA GCCGTGATCA
            247        257        267        277        287        297
         TTATCCTATA GTAACATAAC CTGAAGTATA ACTGACACTA CTATCATCAA TACTTGTCAC
            307        317        327        337        347        357
         ATGAGAACTC TGTGAATAAT TAGGCCACTG AAATTTGATG CCTGAAGGAC CGGCATCACG
            367        377        387        397        407        417
         TATCTTCGAT AAAGCACTTA GTATCACACT AATTGGCTTT TCGCCGCATA TGGTGTTTCC
            427        437        447        457        467        477
         GGTGATTTCC AAGTATTGTT TCCAAGCATC GTACCTTTCA CCATTTGGAG TATCACTTAG
            487        497        507        517        527        537
         CGTTTTCATC GCATATCTGT CCATTATTTC AATGGATTGC CAAATGGAAC TTGATGATG
            547        557        567        577        587        597
         TGAAAGTTTA CTCCTAGCAG TTAACATTTC CACTTCTGTT TCCTCTTTAA TGGCATTCAT
            607        617        627        637        647        657
         TCAACTCTTC CTTGCTTACC GACGTACCCG TATATTGGAA TCTGCGGCCC CAATGACAGA
            667        677        687        697        707        710
         AATCACTGCT TACAATGAAT AAATTGTTCG GATCCTTAAT GTACTCCGAC AAAATATTAC
            727        737        747        757        767        777
         CAATGCAACG ATCAACATCA ACGCTGTTAT GAGAAACCAT CATGGGAATT ACCTTCACCG
            787        797        807        817        827        837
         TATCTAAAGA AATTTCTCTC CATTTCAAAG TTTCCACCAA CATGGGGAGC TGCATCTCTA
            847        857        867        877        887        897
         AGGAATGTTC AGCCATATCA GTGTCATGAT CCATTGGCTT AAACAGCTTC TTTCCGTTCT
            907        917        927        937        947        957
         CAGGATACTC CTTCTGTATT AATGTTTTAC ACAAGTCTGT ATCCACTTTC AGATTACCCA
            967        977        987        997       1007       1017
         AGGGCGTCTC TAGCTCACTG AATGCACTAA CTAAAATTTG GTTTTGAAA TAGATGTGAT
           1027       1037       1047       1057       1067       1077
         GCGACGGCCC CAAGATAAAT ATTCTCTTAA CATTACGGTT CAAATCCAAC GATGCGTACG
           1087       1097       1107       1117       1127       1137
         AGTAGGCCAT AGTGGGTCCA CAATACCTGT AACCGGCATG AGGACATATG ATAATTCTGG
           1147       1157       1167       1177       1187       1197
         CGTTGTGAAT TGGGCCTTTA AGGGTACTTT TGATCAAGTA TGTATGCGGT TGTTGAGATA
           1207       1217       1227       1237       1247       1257
         ATTCTTGGGC TCTATTGGAA TACCATGAGC CTGCATGTGT TGCTGGACGT ATTGACATGT
           1267       1277       1287       1297       1307       1317
         TTGAAAAATT CTATTCTTTG CACTGTAGTC CACCTAAGCC ACCGACTAGG ACCACTTCAC
           1322
         TTAAG
```

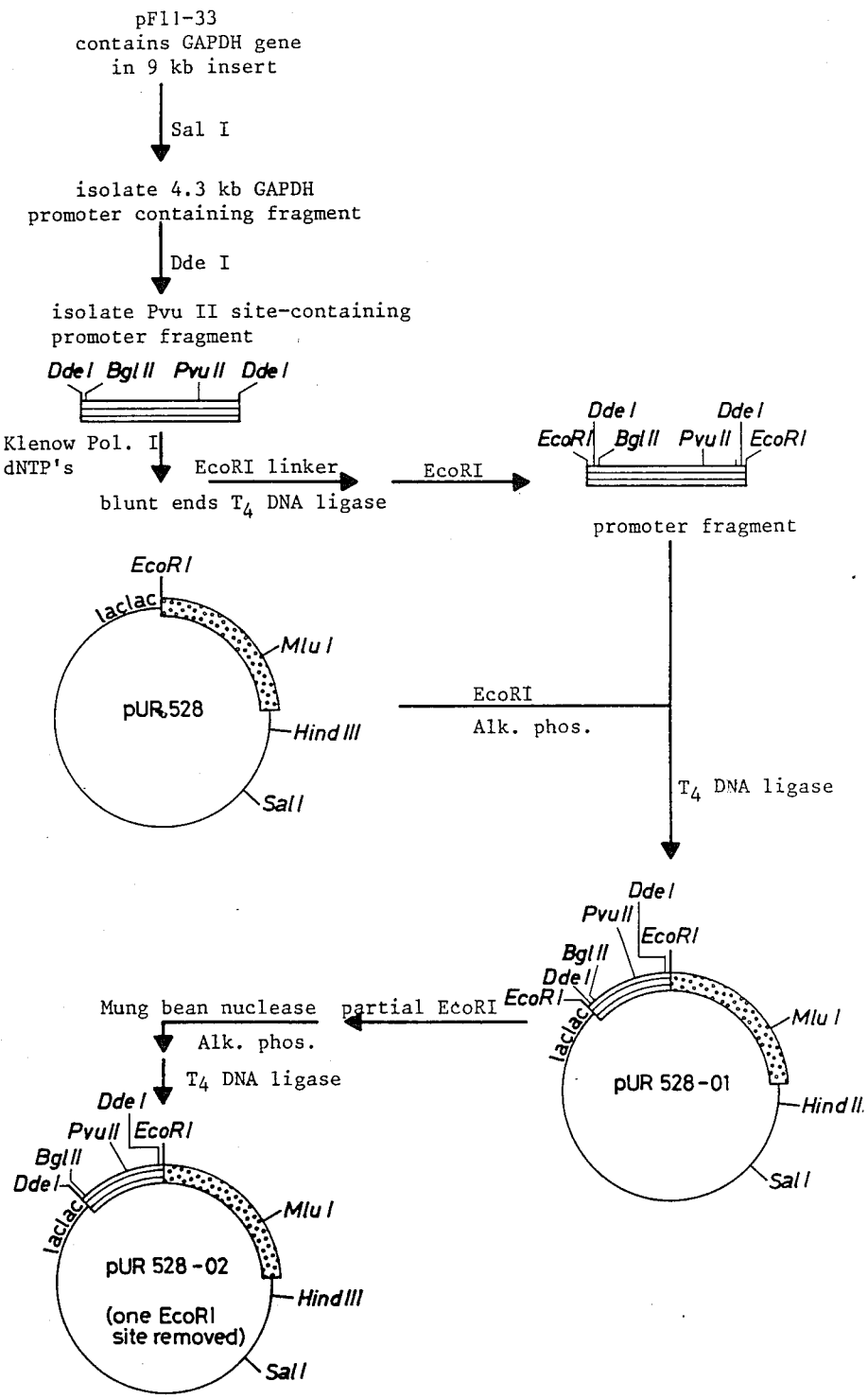

Figure 9

Sac I
5' CCC.TTA.GTT.TCA.AAT.TAA.AGA.GCT.CAT.CAC 3'
                    3' TCT.CGA.GTA.GTG.TGT.TTG.TTT.GTT.TTG.TTT 5'

Klenow DNA-polymerase
                          dNTP's

Dde I              Sac I
5' CCC.TTA.GTT.TCA.AAT.TAA.AGA.GCT.CAT.CAC.ACA.AAC.AAA.CAA.AAC.AAA 3'
3' GGG.AAT.CAA.AGT.TTA.ATT.TCT.CGA.GTA.GTG.TGT.TTG.TTT.GTT.TTG.TTT 5'

Dde I
                   Sac I
  5' TTA.GTT.TCA.AAT.TAA.AGA.GCT.CAT.CAC.ACA.AAC.AAA.CAA.AAC.AAA 3'
     3' CAA.AGT.TTA.ATT.TCT.CGA.GTA.GTG.TGT.TTG.TTT.GTT.TTG.TTT 5'

Sac I

T₄ DNA-polymerase, dNTP's

T₄ DNA ligase

5' TTA.GTT.TCA.AAT.TAA.AGC.ATC.ACA.CAA.ACA.AAC.AAA.ACA.AA 3'
   3' CAA.AGT.TTA.ATT.TCG.TAG.TGT.GTT.TGT.TTG.TTT.TGT.TT 5'

Figure 11

Analysis of $^{35}$S-labeled proteins from K. lactis SD11 cells transformed with pURK 528-03.
K. lactis SD11 cells were grown in the presence of $^{35}SO_4^{2-}$. The labeled cells were converted to protoplasts and the proteins were immunoprecipitated and analyzed on PAA-gels as described by L. Edens et al., Gene 18 (1982), 1.

Lane 5:
Immunoprecipitated $^{35}$S-labeled proteins from K. lactis SD11 cells transformed with plasmid pEK2-7.

Lane 7:
Radioactively labeled merker proteins (Amersham).

Lane 8:
Immunoprecipitated $^{35}$S-labeled proteins from K. lactis SD11 cells transformed with plasmid pURK 528-03.

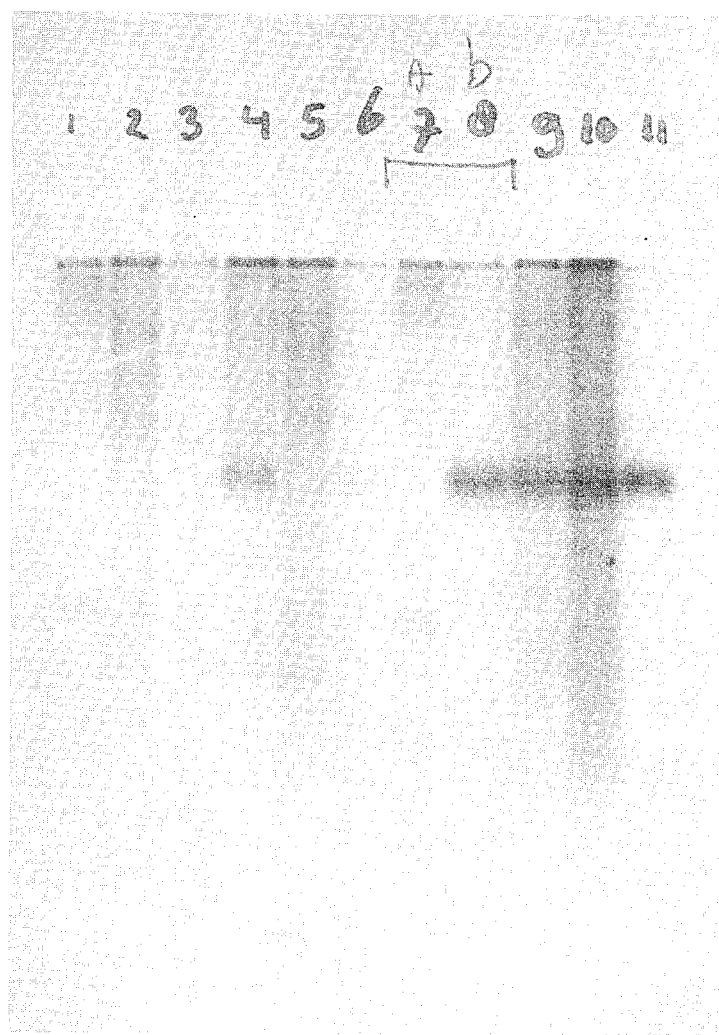

CLONING SYSTEM FOR KLUYVEROMYCES SPECIES

FIELD OF THE INVENTION

This invention relates to the field of recombinant DNA biotechnology. It particularly relates to the use of recombinant DNA biotechnology in the production of polypeptides. More particularly, the present invention relates to new recombinant DNA cloning vehicles and suitable host organisms therefor, which can be used for the high yield production of polypeptides, e.g. enzymes such as beta-galactosidase (lactase) and chymosin and its precursors.

BACKGROUND OF THE INVENTION

In the past few years, microorganisms have proved to be capable of producing foreign peptides and proteins, encoded by foreign genes artificially introduced by means of a transformation system and expressed under the control of regulatory sequences.

Some of the basic techniques for this procedure have been disclosed in, for example, U.S. Pat. No. 4,237,224.

The basic constituents of recombinant DNA technology are formed by:

the gene encoding the desired property and provided with adequate control sequences required for expression in the host organism, a vector, usually a plasmid, into which the gene can be inserted to guarantee stable replication and a high level of expression of the said gene, a suitable host microorganism into which the vector carrying the said gene can be transformed and having the cellular systems to express the information of the said gene.

Amongst the products thus formed are enzymes, hormones, antigens and other useful peptides and proteins.

Some of these products are used as pharmaceutical agents, e.g. growth hormone and interferon, others as auxiliaries in the food industry e.g. beta-galactosidase (lactase), chymosin and amyloglucosidase, and still others may act as biological catalysts for the conversion of certain compounds.

Every contamination of pharmaceuticals or food with harmful organisms or substances should be excluded. The host organisms should also be harmless to persons handling the microbes during experimentation or large scale production processes. Therefore, a prerequisite for the host is that it is not pathogenic.

The first years of recombinant-DNA work were characterized by stringent rules and restrictions to prevent or limit undesired side effects, especially the uncontrolled dissemination of pathogenic microorganisms in the environment.

Although the concern about the supposed risks seems to have been exaggerated, there still remains a steady need for hosts which are not associated with any noxious effect.

Up to now, commercial efforts involving recombinant genetic manipulation of plasmids for producing various substances have centered on *Escherichia coli* as a host organism. The main reason is that *E. coli* is historically the best studied microorganism. The first discoveries and inventions made in recombinant DNA technology have been made with *E. coli* as the host.

However, *E. coli* is not the most desirable organism to use for commercial production of substances applied in pharmaceutical and food industry. It may even prove to be unsuitable as a host/vector system in some situations, because of the presence of a number of toxic pyrogenic factors. The elimination of these may often cause problems. Therefore, *E. coli* has only a very limited use as production organism in fermentation industry. Also the proteolytic activities in *E. coli* may seriously limit yields of some useful products.

These and other considerations have led to an increased interest in alternative host/vector systems. The interest is concentrating in particular on the use of eukaryotic systems for the production of eukaryotic products. A continuing demand exists for new hosts which are above any suspicion as production organisms for chemical substances, in particular food-grade and pharmaceutical grade products, and which moreover are suited to large scale fermentations in industry.

The names of many harmless microorganisms are found on the so called GRAS (Generally Recognized as Safe) list. However, only few genetic procedures are known sofar for the cloning and expression of genes in GRAS-organisms.

Amongst the eukaryotic organisms suitable for commercial exploitation yeasts are perhaps the easiest ones to manage. Yeast, especially bakers' yeast, is relatively cheap, easy to grow in large quantities and has a highly developed genetic system.

The term yeast is frequently used to indicate only *Saccharomyces cerevisiae* or bakers' yeast, which is one of the most common and well-known species. It will be understood that the term yeast as used in this specification is meant to indicate all genera and is not restricted to the species *Saccharomyces cerevisiae*.

Recently, it has been disclosed that cells of *Saccharomyces cerevisiae* are susceptible to transformation by plasmids (A. Hinnen et al., Proc. Natl. Acad. Sci. USA 75 (1978), 1929). Success has been had with cloning and expressing in this yeast the bacterial resistance genes for ampicillin, chloramphenicol and kanamycin, but also eukaryotic genes like the lactase gene and the heterologous genes for ovalbumin, leukocyte interferon D and also a Drosophila gene (see review C. P. Hollenberg, Current Topics in microbiology and Immunology, 96 (1982) 119–144).

Up to now, only one other yeast species has been investigated as a host for yeast expression vectors. The *Saccharomyces cerevisiae* leucine gene has been successfully cloned and expressed in *Schizosaccharomyces pombe* (D. Beach, and P. Nurse, Nature 290 (1981) 140–142).

Yeast vectors which have been described to give successful transformation are based on the natural 2 μm (2 micron) plasmid occurring in many strains of *S. cerevisiae* (see e.g. J. D. Beggs, Nature 275 (1978), 104–109), and on the autonomously replicating sequences (ARS) derived from yeast chromosomal DNA (see e.g. K. Struhl et al., Proc. Natl. Acad. Sci. USA 76 (1979), 1035–1039), respectively. Vectors for *Saccharomyces cerevisiae* which can be used for transformation purposes have also been described by C. P. Hollenberg, Current Topics in Microbiology and Immunology, 96 (1982) 119–144.

The transformation of not well characterized or industrial yeast species is severely hampered by the lack of knowledge about transformation conditions and suitable vectors. In addition, auxotrophic markers are often not available or are undesired, precluding a direct selection by auxotrophic complementation.

SUMMARY OF THE INVENTION

It is an object of this invention to provide a yeast vector system capable of expressing an inserted polypeptide coding sequence.

It is a further object of this invention to provide new genetically engineered yeast strains of the genus Kluyveromyces which are capable of producing polypeptides in culture for mass production.

Is is another object of this invention to provide new genetically engineered yeast strains of the genus Kluyveromyces which are capable of producing chymosin and its precursor forms in culture for mass production.

It is still a further object of this invention to provide new genetically engineered yeast strains of the genus Kluyveromyces which are capable of producing lactase in culture for mass production.

It is still another object of this invention to provide processes for the manufacturing of polypeptides and in particular enzymes with Kluyveromyces as producing organism obtained by recombinant DNA techniques.

It is still another object of this invention to provide particular modified kluyveromyces cells for use in production of polypeptides displaying certain enzymatic activities.

These and other objects will be described in more detail in the further specification.

BRIEF DESCRIPTION OF THE FIGURES

FIG. 5 is a partial nucleotide sequence of the insert from plasmid pF1 1-33;

FIG. 6 is a partial nucleotide sequence of the insert from plasmid pF1 1-33;

FIG. 7 is the pathway by which plasmids pUR528-01 and pUR 528-02 are constructed;

FIG. 9 is the pathway for construction of a 38bp double stranded oligomer for insertion between the GAPDH promoter and initiation codon;

FIG. 11 is an autoradiogram of immunoprecipitated proteins produced by K. lactis grown in the presence of $^{35}SO_4^{2-}$. The autoradiogram demonstrates the synthesis of plasmid encoded proteins.

DESCRIPTION OF THE INVENTION

Figure 1:
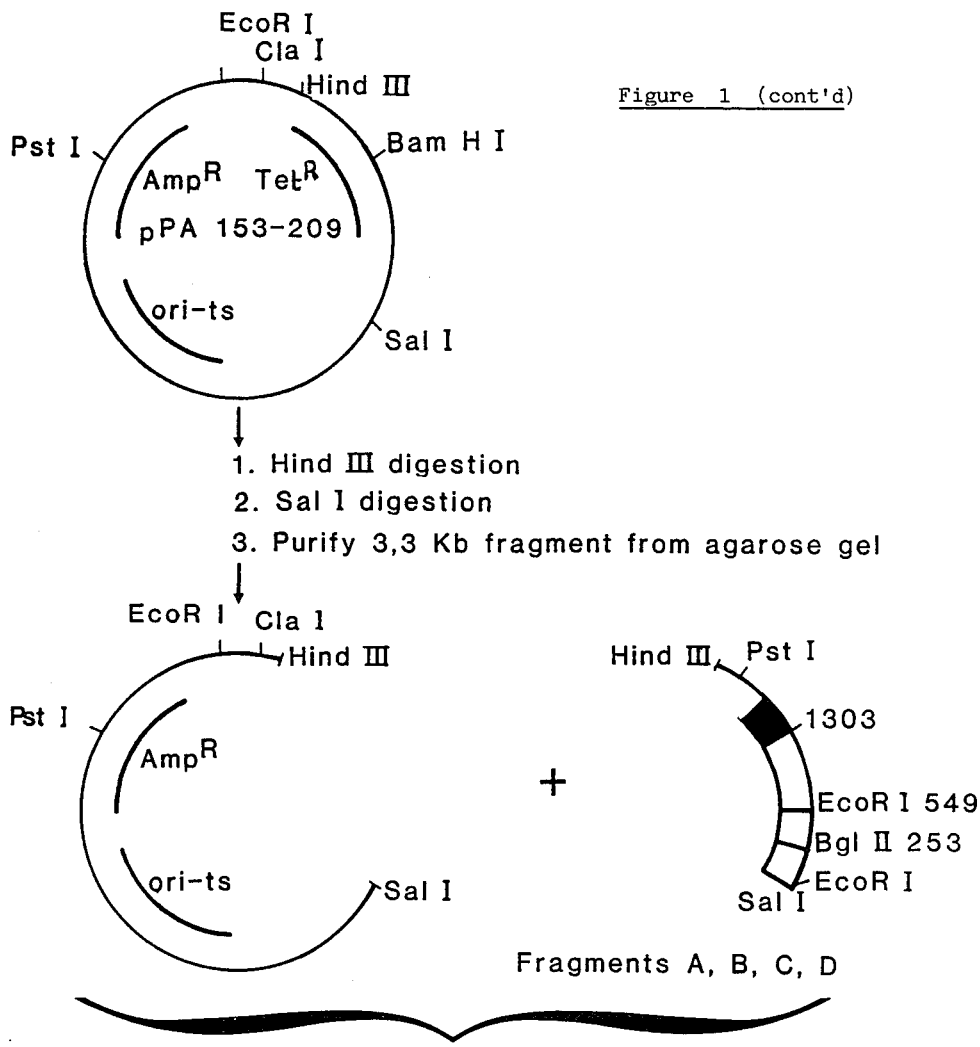
FIG. 1 is the pathway by which plasmids pGB131, pGB122, pGB123 and pGB124 are constructed from plasmids pUR1531, pUR1522, pUR1523, and pUR1524, respectively.

Yeasts of the genus Kluyveromyces and in particular the species *K. lactis* and *K. fragilis* are biotechnologically important and are of commercial interest. *Kluyveromyces lactis* and *Kluyveromyces fragilis,* for example, are used for the commercial production of the enzyme lactase (beta-galactosidase). Kluyveromyces organisms are mentioned on the GRAS-list.

In contrast with most of the bacterial species investigated in transformation experiments, yeast cells possess a cell wall impermeable for plasmids. Therefore, a usual preparatory step of yeast transformation is the removal of the cell wall, yielding protoplasts which are able to take up plasmids. Cell wall lytic enzymes which advantageously may be used are selected from the group of beta-1,3-glucanases. A suitable example is helicase, a crude enzyme preparation originating from gut of the snail *Helix pomatia.* Another suitable representative is zymolyase.

It is well known that the cell wall can be regenerated during subsequent incubation under suitable conditions. However only a fraction of the protoplasts regenerates and for *Kluyveromyces lactis* this process has appeared to be even twenty times less efficient that for *Saccharomyces cerevisiae* under similar conditions.

Although transformation of yeasts using protoplasts has been described by several authors, it appears that some yeast strains and particularly wild type yeast strains and Kluyveromyces species are very difficult to regenerate. Hollenberg described (Current Topics in Microbiology and Immunology, 96 (1982) 119–114), how the regeneration of protoplasts of *Saccharomyces cerevisiae* can also take place if the usual osmotic stabilizer sorbitol is substituted by 0.6M potassium chloride. It has now been surprisingly found that by applying this method to Kluyveromyces protoplasts the fraction of regenerated yeast cells even increases three to fivefold.

Recently, a method has been disclosed by Ito et al (J. Bacteriol. 153 (1983) 163–168), in which whole cells are used instead of protoplasts, thereby circumventing the regeneration step. This method has been shown to be effective in *S. cerevisiae* with certain types of plasmids.

It has now been found that his method is surprisingly effective in Kluyveromyces, particularly when plasmids containing KARS-sequences (as will be described hereinafter) are used.

It will be appreciated by those skilled in the art, that the availability of a suitable vector is of decisive importance. Beforehand it is uncertain if a specific host/vector combination will act successfully as a transformation system. For example, it is known from S. Das and C. P. Hollenberg, Current Genetics 6 (1982) 123–128, that plasmid pMP81 can be transformed into *Saccharomyces cerevisiae* YT6-2-IL (cir°) but not into *Kluyveromyces lactis.* D. Beach and P. Nurse disclosed in Nature 290 (1981) 140–142, that plasmid pJDB219 has a high copy number in *Saccharomyces cerevisiae,* but transforms *Schizosaccharomyces pombe* at the very low frequency of only 2 transformants per microgram DNA.

Up to now vectors for Kluyveromyces were not known at all.

As a result of extensive research and experimentation new vectors were found which are capable of transforming the host organism Kluyveromyces and which, moreover, are able to replicate autonomously in the transformed cell.

The new vectors, which are particularly suitable for Kluyveromyces and preferably for *K. lactis* and *K. fragilis,* can be distinguished in two categories according to the constituting DNA sequences which control the function of replication and maintenance in, for example, Kluyveromyces species viz.:

1. vectors containing autonomously replicating sequences (ARS), and
2. vectors devoid of autonomously replicating sequences but containing homologous Kluyveromyces DNA acting as a site for recombination with the host chromosome.

Suitable and preferred ARS vectors are those originating from Kluyveromyces, also referred to as KARS vectors. Said vectors of the KARS type are preferably used because of their high transformation frequency. Vectors of the second category usually transform with low frequency but they are very stably retained in the host cells.

Preferred vectors of the first category are, for example, KARS vectors originating from *K. lactis*, of which pKARS12 and pKARS2 are the most preferred. pKARS12 and pKARS2 are hybrid plasmids composed of a *K. lactis* DNA fragment containing the KARS12 and KARS2 sequence, respectively which are inserted into the known *S. cerevisiae* plasmid YRp7.

A preferred vector of the second category is, for example, pL4, a hybrid plasmid composed of the plasmid YRp7 carrying the ARS1 sequence and a *K. lactis* XhoI DNA fragment carrying the LAC4 gene.

For transformation purposes in Kluyveromyces the following genes can, for example, be advantageously used as selectable markers on the vectors:

1. the tryptophan gene (TRP1) derived from *S. cerevisiae*;
2. the lactase gene (LAC4) derived from *K. lactis*;
3. the $Kan^R$ gene coding for resistance against the antibiotic G418 which is related to gentamycin, derived from *E. coli*.

On the vectors there are suitable restriction sites which allow further gene cloning.

The stability of the transformed plasmids may considerably be enhanced if a centromere region (CEN) from the *K. lactis* or *S. cerevisiae* chromosome is inserted in the vector.

Also *Escherichia coli* is a suitable host, especially for cloning and storage. In that case the ampicillin resistance gene ($Amp^R$) is also a suitable selectable marker on the vector. The plasmids are preferably multiplied and stored within *E. coli* cells, particularly those of the strains DG75 and JA221. The transformed strains are selectively grown on L-broth containing:

kanamycin (20 μg/ml) for *E. coli* DG75 (PTY75-LAC4), and ampicillin (100 μg/ml) for *E. coli* DG75 (pL4) and *E. coli* JA221 (pKARS12).

Said transformed strains were deposited under Rule 28, resp. 28a of the European Patent Convention with the Centraal Bureau voor Schimmelcultures, Oosterstraat 1, 3742 SK Baarn, the Netherlands under numbers CBS 351.82 (=LMD 82.18), CBS 352.82 (=LMD 82.19) and CBS 353.82 (=LMD 82.20), respectively, on 19th May 1982. The plasmids can be isolated from the cells, e.g. by the method of L. Katz et al., J. Bacteriol. 114 (1973) 577.

The protoplasts of the yeast host are transformed by the aforementioned vectors in a usual incubation medium containing Tris, calcium chloride and polyethylene glycol having a molecular weight ranging from 2000 to 6000, but preferably of 4000.

Prokaryotic transformants can easily be detected by well-known means of primary selection. Even if the desired property is not recognizable in the phenotype of the transformant, the vector usually contains one or more genes coding for primary selectable properties like antibiotic resistance or genes coding for essential growth factors. In the latter case the corresponding auxotrophic mutant of the host should be available. While there are many auxotrophic prokaryotes available, the number of auxotrophic industrial yeasts is limited. Mutation of a gene from a production strain often adversely affects important growth and production characteristics of that strain.

The transformation method according to this invention, using whole cells instead of protoplasts for the transformation of Kluyveromyces species, can be suitably performed as follows.

The method according to the invention comprises growing Kluyveromyces cells in standard yeast medium and harvesting the cells at $OD_{610}$ nm between 1 and 25. Optimal results are obtained at $OD_{610}$ nm between 4 and 10.

The Kluyveromyces cells are washed and pretreated with certain types of chaotropic ions, e.g. $Li^+$, $Cs^+$, $Rb^+$. LiCl and $Li_2SO_4$ are conveniently used, at final concentrations of about 20 mM–0.2M, preferably about 0.1M.

The Kluyveromyces cells are incubated with said monovalent ions at 30° C. for about 5–200 minutes, usually about 60 min. followed by an incubation with DNA. The transformation can be enhanced if subsequently polyethylene glycol is added. Generally, an equal volume of 70% polyethylene glycol 7000 is used. The Kluyveromyces transformation can be further enhanced by exposing the cells to a heat treatment. For example, by a treatment for about 5 minutes at about 42° C., the enhancement is about 20-fold.

The use of this procedure according to the invention will be shown in detail in the Examples with *Kluyveromyces lactis* SD11, *Kluyveromyces fragilis* leu 24 and *Kluyveromyces fragilis* C21 as respective host organisms.

In contrast to prokaryotes, the use of antibiotic resistance markers in yeast is far from easy. Only a small number of antibiotics is active against yeast. Moreover, the resistance factors predominantly originate from bacteria and it is not at all obvious if they can be expressed in yeast cells and used as a selective marker.

Kanamycin and the aminoglycoside G418 which is related to gentamycin have been shown to be poisonous for cells of wild type yeast strains.

It is further known from Hollenberg, Extrachromosomal DNA, ICN-UCLA Symp. (1979) 15: 325–338, Acad. Press, New York, that the transposable resistance element Tn601 (present on bacterial plasmid pCR1) contains a gene that confers resistance to kanamycin to transformants of *Saccharomyces cerevisiae*. A. Jimenez and J. Davis, Nature 287 (1980) 869–871, showed later that the kanamycin resistance gene can also confer resistance to *S. cerevisiae* transformants against antibiotic G418, a potent inhibitor of yeast growth.

The plasmid PTY75-LAC4, a hybrid plasmid composed of the plasmid pCR1, the 2 μm plasmid from *S. cerevisiae* and the Sal I fragment from plasmid pK16, carrying the *K. lactis* LAC4 gene and forming also a feature of the present invention, contains the same resistance gene. It has now been found that this gene is expressed also in *Kluyveromyces lactis*, enabling the strain to inactivate G418 taken up from the growth medium and providing thus a tool for primary selection of *Kluyveromyces lactis* transformants.

Although plasmid PTY75-LAC4 does not contain any autonomously replicating sequence from Kluyveromyces, it was surprisingly found that plasmids containing the 2 μm plasmid from *S. cerevisiae*, such as PTY75-LAC4, do replicate autonomously in Kluyveromyces species.

Selection of G418 resistant yeast cells transformed by PTY75-LAC4 was performed on regeneration plates containing glucose, sorbitol and 0.2 mg/ml G418. KCl is not suited here because, due to high salt concentration, *Kluyveromyces lactis* cells are insensitive to G418, even in concentrations up to 0.8 mg per ml.

Resistant colonies appear within 5–6 days after transformation with PTY75-LAC4. Real transformants can be distinquished from colonies which have become resistant by spontaneous mutation by checking the presence of PTY75-LAC4 DNA by colony hybridisation with labelled pCR1 DNA, or, in case a *K. lactis* lac4 mutant is used as host strain, by checking their ability to grow on minimal medium (yeast nitrogen base, Difco) with lactose as the sole carbon source. On the average, 5% of the resistant colonies were found to contain PTY75-LAC4 DNA or to be Lac+. By this method of selection about 4 transformants per microgram of plasmid DNA were obtained.

Direct selection in *K. lactis* SD69 lac4 for the presence of the LAC4 gene, using plates containing lactose as sole carbon source and 0.6M KCl as osmotic stabilizer, yielded 20 Lac+ transformants after 4 to 5 days of incubation at 30° C. On control plates without DNA no Lac+ colonies were found to appear within said period. The Lac+ colonies of the direct selection were shown to be transformants and not spontaneous revertants, because the presence of the Kan$^R$ marker on G418 plates could be demonstrated as described above.

When plasmid pL4 (cf. Example 3) or KARS-type plasmids are used, one also has the possibility of selecting for the presence of tryptophan prototrophy in the transformants. In comparison with plasmid pTY75-LAC4, the use of plasmid pL4 caused a substantial increase in the efficiency of transformation: 30 transformants per microgram DNA were found. The KARS-type plasmids, however, having $10^3$–$10^4$ transformants per microgram DNA appear to be far superior.

The plasmid PTY75-LAC4 and KARS-containing plasmids were found to exist in transformed cells autonomously replicating. This was demonstrated with the aid of DNA analysis. Undigested minilysates of transformants were analyzed according to the Southern blot procedure, by hybridization with 32p-labelled pCR1, the bacetrial component of plasmid PTY75-LAC4 or with labelled pBR322, the bacterial part of the pKARS plasmids.

Comparative electrophoresis of a minilysate of an untransformed *Kluyveromyces lactis* lac4 trp1 mutant and of purified plasmid preparations shows that only in the transformants hybridizing bands are present with electrophoretic mobilities corresponding to supercoiled and open circular forms of the plasmid used for transformation.

Presence of the plasmid in transformed cells was further confirmed by transforming *E. coli* with the DNA preparation from the yeast transformants and isolating the same plasmids from the *E. coli* transformants formed.

The process of the present invention can be applied to host strains of the species *Kluyveromyces lactis* as well as to strains of the species *Kluyveromyces fragilis*. Both species are safe organisms and appear on the GRAS-list.

Particularly useful hosts are the mutants *Kluyveromyces lactis* SD11 lac4 trp1 and SD69 lac4 which are derived from the wild type CBS 2360 and deposited under Rule 28, resp. 28a of the European Patent Convention with Centraal Bureau voor Schimmelcultures, Oosterstraat 1, 3742 SK Baarn, Netherlands, under numbers CBS 8092 and CBS 8093, respectively, on 19th May 1982. Usually, transforming plasmids remain within the host cell as separate entities capable of autonomous replication and expression. It is pointed out here, however, that genes, after having been introduced on plasmids (with or without replication sequences) can subsequently also be integrated in the chromosomal DNA of the cell.

This so-called integrative transformation appeared to have occured in stable *K. lactis* SD11 trp1 Lac+ transformants after transformation with plasmid pL4. In this case no free plasmid DNA is present in the transformants. Integration of the LAC4 gene can be demonstrated by Southern blot DNA analysis of the total cell DNA that is digested by restriction enzymes, the pL4 plasmid functioning as a labelled hybridization probe.

To maintain the plasmids in the yeast transformants the following selective media can be used, for example: yeast nitrogen base medium (DIFCO) plus 2% lactose instead of glucose for *K. lactis* SD69 lac4 PTY75-LAC4) and for *K. lactis* SD69 lac4 (pL4) and yeast nitrogen base medium (DIFCO) plus 2% glucose for *K. lactis* SD11 lac4 trp1 (pKARS12).

Hybride plasmids have been constructed comprising KARS12-LAC4 and KARS12-2 μm DNA-LAC4 sequences. When the new microorganisms according to the invention are used for large scale production, it is desirable to remove all bacterial DNA sequences from the vector plasmids.

Genes can remain on autonomously replicating plasmids after having been introduced into the cell or may be integrated in the chromosomal DNA of the host cell.

The invention can be used for the cloning and expression of both prokaryotic and eukaryotic genes in Kluyveromyces as a host, preferably using a plasmid vector of one of the types as described hereinbefore. Suitable prokaryotic genes for use according to the invention are, for example, those coding for lactase, alpha-amylase, amyloglucosidase and beta-lactamase. Suitable eukaryotic genes for use according to the invention are, for example, those coding for lactase, chymosin, invertase and interferon. For the insertion of the genes coding for these products suitable restriction sites are available on the vectors as described hereinbefore.

According to this invention, prokaryotic and eukaryotic genes, both homologous and heterologous, can be used. The invention can advantageously be used for the high production of chemical substances, in particular polypeptides. A preferred embodiment of the invention is the production of chymosin, a milk clotting enzyme.

The choice of the vector and regulons for the cloning and expression of genes in Kluyveromyces may, of course, vary with the gene used in a particular case. Also, the choice of a particular Klyveromyces strain as a host and the optimal process conditions may vary with, inter alia, the gene and vector to be selected. The optical selection and process conditions can be established by routine experimentation. These variations are all included within this invention.

The invention is further exemplified by a detailed description of the cloning and expression of:

a. a homologous gene, beta-galactosidase (lactase), in *K. lactis;* b. a prokaryotic heterologous gene, $Kan^R$, in *K. lactis* and *K. fragilis;* c. a eukaryotic heterologous gene, TRP1, in *K. lactis;* d. a eukaryotic heterologous gene, LEU2, in *K. fragilis;* e. a eukaryotic heterologous gene, encoding preprochymosin and its maturation forms, in *K. lactis;* and f. a eukaryotic heterologous gene, encoding prepro-thaumatin and its maturation and modified forms, in *K. lactis.*

The following Examples illustrate certain embodiments of the present invention.

EXAMPLE 1

Recombinant plasmid PTY75-LAC4

0.5 μg of the plasmid pK16 described by R. Dickson, (Gene 10 (1980) 347-356) and 0.5 μg of the plasmid PTY75 described by C. P. Hollenberg et al. (Gene 1 (1976) 33-47) were digested with the restriction enzyme Sal I. The two digests were mixed and after inactivation of the restriction enzyme the solution was incubated with T4-ligase, yielding a solution with recombinant DNA.

This ligated mixture ws used to transform to the *E. coli* strain DG75 (hsdS1 leu-6 ara-14 galK2xyl-5 mt-1 rpsL20 thi-1 supE44-λ-lac Δz 39) according to R. C. Dickson et al., Cell 15 (1978) 123-130, resulting in kanamycin resistance ($Kan^R$). $Kan^R$ colonies were further selected on supplemented minimal plates, containing lactose as the sole carbon source, for the formationof Lac+ colonies. The plasmid PTY75-LAC4 was isolated from one of the selected $Kan^R$ Lac+ transformants, using the method according to L. Katz et al., J. Bacteriol. 114 (1973) 577-591.

EXAMPLE 2

Recombinant pKARS plasmids

5 μg of plasmid YRp7 (Struhl et al., Proc. Natl. Acad. Sci., 76 (1979) 1035-39) were digested with restriction enzyme Sal I. 14 μg of DNA from the wild strain *K. lactis* CBS 2360 were digested with enzyme Xho I. The fragments of the plasmid and the *K. lactis* DNA were mixed in a molar ratio of 1:3. After inactivation of the restriction enzymes the solution was brought to a DNA concentration of 25 μg/ml and incubated with T4-ligase under standard conditions (Boehringer).

Transformation of *E. coli* DG75 with the ligated mixture under usual conditions yielded a mixture of $4.5 \times 10^5$ $Amp^R$ transformants, $9 \times 10^3$ of which contain *K. lactis* inserts, as can be deduced from their sensitivity to tetracyclin. The proportion of tetracyclin-sensitive cells can be increased to 85% by cycloserine treatment, see F. Bolivar and K. Backman, Methods in Enzymology 68 (1979) 245-267. According to the method of Katz et al. (see Example 1) 14 different plasmids were isolated, which are referred to as pKARS 1-14. All were capable of transforming *K. lactis* SD11 lac4 trpl strain to Trp+ phenotype with a frequency of $10^3$-$10^4$ per microgram of DNA. Plasmid pKARS12 showed the highest transformation frequency of $3 \times 10^4$ per microgram of DNA, but plasmid pKARS2 appeared to be more convenient in further processing.

The recombinant plasmids obtained could also be transferred to *E. coli* JA221 (Δ trp E5, leu B6, lac y, rec A, hsdM+, hsdR−).

EXAMPLE 3

Recombinant plasmid pL4

A mixture of YRp7 and *K. lactis* DNA fragments was prepared as described in Example 2. *E. coli* DG75 strain was transformed with the ligated mixture and subsequently plated on M9 minimal agar, the medium of which contained lactose as the sole carbon source, to which leucine had been added. Lac+ colonies appeared after 8 days at 30° C. Plasmid pL4 was isolated from one of these Lac+ colonies using the method of Katz et al. (see Example 1).

EXAMPLE 4

*Kluyveromyces lactis* SD69 lac4 transformed to $G418^R$ lac4+ with plasmid PTY75-LAC4

Cells of the *Kluyveromyces lactis* mutant SD69 lac4 were suspended in a growth medium (pH 6.8) containing 1% of yeast extract, 2% of peptone and 2% of glucose. The growth was continued until the exponential phase ($3-5 \times 10^7$ cells per ml) had been reached.

The yeast cells were collected by centrifugation, washed with water and resuspended in a solution (pH 8.0) containing 1.2M sorbitol, 25 mM EDTA and 0.2M fresh mercaptoethanol. After incubation for 10 min. at 30° C. the cells were centrifuged, washed two times with a 1.2M sorbitol solution and resuspended in 20 ml of a solution (pH 5.8) containing 1.2M sorbitol, 10 mM EDTA, 0.1M sodium citrate and 10 mg helicase.

Protoplasts were formed and after 15-20 min. these were centrifuged, washed three times with 1.2M sorbitol and resuspended to a concentration of about $5.10^{10}$ cells per ml in 0.1 ml of a solution containing 10 mM $CaCl_2$ and 1.2M sorbitol.

10 μg of pTY75-LAC4 were added and the mixture was incubated for 15 min at 25° C. Thereafter 0.5 ml of a solution (pH 7.5) containing 10 mM Tris, 10 mM $CaCl_2$ and 20% (w/v) polyethylene glycol 4,000 was added, followed by 20 minutes incubation.

Protoplasts were precipitated by centrifugation and then resuspended to a concentration of about $5 \times 10^{10}$ protoplasts per ml in a solution (pH 6.8) containing 7 mM $CaCl_2$, 1.2M sorbitol, 0.5 mg/ml yeast extract, 1 mg/ml peptone and 2 mg/ml glucose.

After incubation for 60 min. at 30° C. the protoplasts were centrifuged, washed with 0.6M KCl solution and resuspended in 0.6M KCl solution.

In order to be able to select the G418 resistant transformants, $1 \times 10^9$ protoplasts were plated in a 3% agar overlay on 2% minimal agar plates containing 2% of glucose, 1.2M sorbitol and 0.2 mg/ml of the antibiotic G418. For the purpose of simultaneously selecting Lac+ transformants, $5 \times 10^8$ protoplasts were plated in 3% agar overlay on 2% minimal agar plates, DIFCO yeast nitrogen base medium, containing 2% lactose as the sole carbon source and 0.6M KCl instead of 1.2M sorbitol.

Colonies appeared within 4-5 days. On sorbitol plates without G418 protoplast regeneration was usually 0.2-0.5%, whereas on the 0.6M KCl plates with glucose as carbon source this percentage increased to 0.5-1.5%.

When G418 was used for the selection, one transformant was obtained per $10^7$ regenerated protoplasts. Simultaneous selection on lactose plates yielded 10 transformants per $10^7$ regenerated protoplasts or 20 transformants per microgram of plasmid DNA.

The presence of PTY75-LAC4 in the yeast cells could be proved by means of the Southern hydridization method with $^{32}$P-labelled pCR1.

DNA preparations were made according to Struhl et al. (Proc. Natl. Acad. Sci. 76 (1979) 1035–1039).

EXAMPLE 5

*Kluyveromyces lactis* SD11 lac4 trpl transformed to Trp+ with plasmid pKARS12

Cells of the strain *K. lactis* SD11 lac4 trpl were transformed as described in Example 4 with 10 μg of pKARS12 DNA. Transformants were selected on 2% minimal agar plates containing 2% of glucose and 0.6M KCl. Per microgram of pKARS12 DNA $3.4 \times 10^4$ Trp+ transformants were obtained.

EXAMPLE 6

*Kluyveromyces lactis* SD69 lac4 transformed to Lac+ with plasmid pL4

*K. lactis* strain SD69 lac4 was transformed with plasmid pL4 using the same method as described for PTY75-LAC4 in Example 4. The transformants were selected on yeast nitrogen base plates (DIFCO) containing 2% of lactose. The transformation frequence was 20 transformants per microgram of plasmid DNA.

EXAMPLES 7–13

*Kluyveromyces lactis* transformed with KARS-type plasmids.

Analogous to the method described in Example 5, transformation experiments were carried out with other KARS-type plasmids. The results of the experiments are summarized in the following Table for comparison the result of the experiment described in example 4 is also mentioned.

TABLE

| Ex. | Strain | Genotype | Plasmid | Transformants per microgram DNA | Size of KARS fragments (kb) |
|---|---|---|---|---|---|
| 4. | SD69 | lac4 | PTY75-LAC4 | 20 | — |
| 7. | SD11 | lac4 trpl | pKARS1 | $1.5 \times 10^3$ | 2.24 |
| 8. | SD11 | lac4 trpl | pKARS2 | $5 \times 10^3$ | 1.24 |
| 9. | SD11 | lac4 trpl | pKARS7 | $10^3$ | 2.3 |
| 10. | SD11 | lac4 trpl | pKARS8 | $5 \times 10^3$ | 1.85 |
| 11. | SD11 | lac4 trpl | pKARS10 | $2.4 \times 10^4$ | 3.15 |
| 5. | SD11 | lac4 trpl | pKARS12 | $3.4 \times 10^4$ | 5.0 |
| 12. | SD11 | lac4 trpl | pKARS13 | $1.5 \times 10^4$ | 2.0 |
| 13. | SD11 | lac4 trpl | pKARS14 | $1.8 \times 10^4$ | 2.15 |

The molecular weights of pKARS plasmids were determined after digestion with endonucleases Eco RI and Hind III, using 0.8% of agarose gel and the usual molecular weight markers.

EXAMPLE 14

*Kluyveromyces lactis* SD11 lac4 trpl transformed to Trp+ with plasmids containing the KARS-2 sequence using a transformation procedure with whole cells Plasmid pEK2-7 was used to transform *K. lactis* SD 11. This plasmid consists of the well-known plasmid YRp7 into which a 1.2 kb fragment containing the autonomously replicating sequence derived from KARS-2 has been cloned (FIG. 2). *K. lactis* SD11 was grown overnight at 30° C. in a medium containing 1% yeast extract, 2% peptone and 2% glucose (pH 5.3). The cells were harvested at OD$_{610}$ nm of 4–8 by centrifugation at $1000 \times g$ for 5 minutes. The cells were washed with TE-buffer (10 mM Tris-HCl, 1 mM EDTA, pH 8.0) and the pellet was resuspended in TE-buffer at a concentration of $2 \times 10^8$ cells per ml. This suspension was diluted with one volume of 0.2M LiCl and shaken at 30° C. for 60 minutes. Plasmid pEK2-7 DNA (10 μg) was added to 0.1 ml of Li-treated cells and the incubation was continued at 30° C. for 30 min. One volume of 70% polyethylene glycol 7000 was added and the mixture was incubated for another 60 minutes at 30° C. The mixture was exposed to heat treatment at 42° C. for 5 minutes and the cells were washed with sterile, demineralized water. Cells were plated onto minimal agar containing 2% glucose and 0.67% yeast nitrogen base. Transformants were observed after 36–48 hours at 30° C.

EXAMPLE 15

*Kluyveromyces fragilis* transformed with plasmids containing the KARS-2 sequence Two types of plasmids were used to transform *K. fragilis*. The first plasmid pGB 180 was constructed by cloning the 3.5 kb Bgl II fragment from plasmid pEK2-7 (FIG. 2) containing the KARS-2 autonomously replicating sequence from *K. lactis* and the TRP1 gene from *S. cerevisiae* into the Bam H1 site of pJDB 207 (J. D. Beggs, Alfred Benzon Symposium 16 (1981) 383). About 36 *K. fragilis* leu mutants obtained after UV-treatment of *K. fragilis* were transformed with pGB 180 by the Li+ method as described in Example 14. One mutant, *K. fragilis* leu 24, was transformed to Leu+ with a frequency of about $10^3$ transformants per ug of plasmid DNA. The second plasmid, pGL2, was constructed by cloning the 3.5 kb BglII fragment from pEK2-7 as described above into the Bam Hl site of the well-known plasmid pACYC177, Chang et al., J. Bacteriol. 134 (1978), 1141–1156, which contains the transposon Tn601 conferring resistance to kanamycin and the gentamycin derivative G418. *K. fragilis* strain C21 was transformed with plasmid pGL2 by the Li+ method as described in Example 14. The transformed cells were plated onto YNPD-agar containing 50 μg of G418 per ml. Transformants were detected after incubation at 30° C. for 48 hours, whereas spontaneous resistant mutants were detected only after 6 days. DNA was extracted from *K. fragilis* transformants and transformed into suitable *E. coli* DG 75 cells. DNA extracted from kanamycin-resistant *E. coli* cells showed the presence of plasmid pGL2. These experiments show that *K. fragilis* strains can be transformed by plasmids containing KARS-sequences and that these plasmids are autonomously replicating in *K. fragilis*.

EXAMPLE 16

*Kluyveromyces lactis* SD11 lac4 trpl expressing preprochymosin and its various maturation forms after being transformed with plasmids containing the KARS-2 sequence, the structural genes encoding preprochymosin and its various maturation forms, and various promoters directing the syntheses of said structural genes.

This Example comprises a number of steps the most essential of which are:

1. Addition of Sal I linkers in front of the cloned structural genes encoding preprochymosin, prochymosin, pseudochymosin and chymosin.
2. Introduction of a DNA fragment in plasmids obtained above containing the KARS-2 autonomously replicating sequence from *K. lactis* and the TRP1 gene from *S. cerevisiae*.

3. Introduction of various promoters into the plasmids obtained above directing the synthesis of the various maturation forms of preprochymosin.

Starting materials for the expression of bovine preprochymosin and its various maturation forms in *K. lactis* were the following cloned structural genes
methionyl-pseudochymosin, described as pUR 1531
methionyl-chymosin, described as pUR 1522
methionyl-prochymosin, described as pUR 1523
methionyl-preprochymosin, described as pUR 1524

The construction and structure of these plasmids have been described in detail in European Patent Application No. 82201272.0, published on Apr. 20, 1983 under No. 0077109. These genes were isolated and these plasmids constructed according to the said description.

A. Introduction of Sal I linkers in plasmids pUR 1531, pUR 1522, pUR 1523 and pUR 1524 (FIG. 1)

The plasmids pUR 1531, pUR 1522, pUR 1523 and pUR 1524 contain an Eco RI restriction site just in front of the ATG initiation codon. Because an additional Eco RI site is present within the chymosin gene, it was aimed to introduce a Sal I linker molecule just in front of the first Eco RI site to facilitate the introduction of various promoter sequences directing the expression of the distal structural genes.

About 50 μg of DNA was incubated with 50 units of endonuclease Eco Rl in the presence of 125 μg/ml ethidiumbromide in 10 mM Tris-HCl, 50 mM NaCl, 6 mM beta-mercaptoethanol, 10 mM MgCl₂ and 100 μg/ml bovine serum albumin, pH 7.5, at 37° C. for 60 minutes. Plasmid DNA were predominantly converted to linear and open circular molecules under these conditions. The DNA was extracted with one volume of phenol and one volume of chloroform and precipitated with one volume of propanol-2. The DNA was dissolved in TE-buffer and completely digested with endonuclease Sal I. A DNA fragment of about 1800 bp was isolated from agarose gel by electroelution.

The fragments were extracted with phenol and chloroform and precipitated with propanol-2. The precipitates were dissolved in TE-buffer. The cohesive ends were filled-in with DNA polymerase as follows: To 15 μl containing the 1800 bp DNA fragment (about 1–2 μg) was added 1 μl of a 2 mM solution of dATP, dGTP, dCTP and dTTP, 6.5 μl of 4x nick-buffer containing 0.2M Tris-HCl (pH 7.2), 40 mM MgSO₄, 4 mM dithiothreitol and 200 mg/ml bovine serum albumin, and 2.5 μl of water. Two units of DNA polymerase (Klenow fragment) were added and the mixture was incubated at 20° C. for 30 minutes. DNA polymerase was then inactivated by heating at 70° C. for 5 minutes. A phosphorylated Sal I-linker (prepared as described in Maniatis et al, Molecular Cloning, CSH) was added to this mixture together with T4 DNA ligase (10³ Units) and ATP. After incubation at 22° C. for 4 hours the mixture was incubated at 4° C. for an additional 16 hours. The mixture was then incubated with endonucleases Sal I and Hind III and a DNA fragment of about 1500 bp was recovered from an agarose gel by electroelution. The fragments (A,B,C,D) were purified by phenol and chloroform extraction and precipitation with propanol-2. These fragments were ligated to 3.3 kb Hind III-Sal I fragment (about 0.5 μg) derived from plasmid pPA153-209 containing a temperature-sensitive replicon and an ampicillin resistant gene (encoding beta-lactamase), and purified by electroelution. The ligated molecules were transformed into *E. coli* HB 101 and ampicillin resistant, tetracyclin sensitive clones were cultured and plasmid DNA extracted. Digestion of plasmid DNA with endonuclease Sal I, Eco Rl and Hind III confirmed that the plasmids pGB131, pGB122, pGB123 and pGB124 (FIG. 1) were obtained.

B. Introduction of a KARS2 and TRP1 gene in the plasmids pGB131, pGB122, pGB123 and pGB124, respectively.

Figure 2:
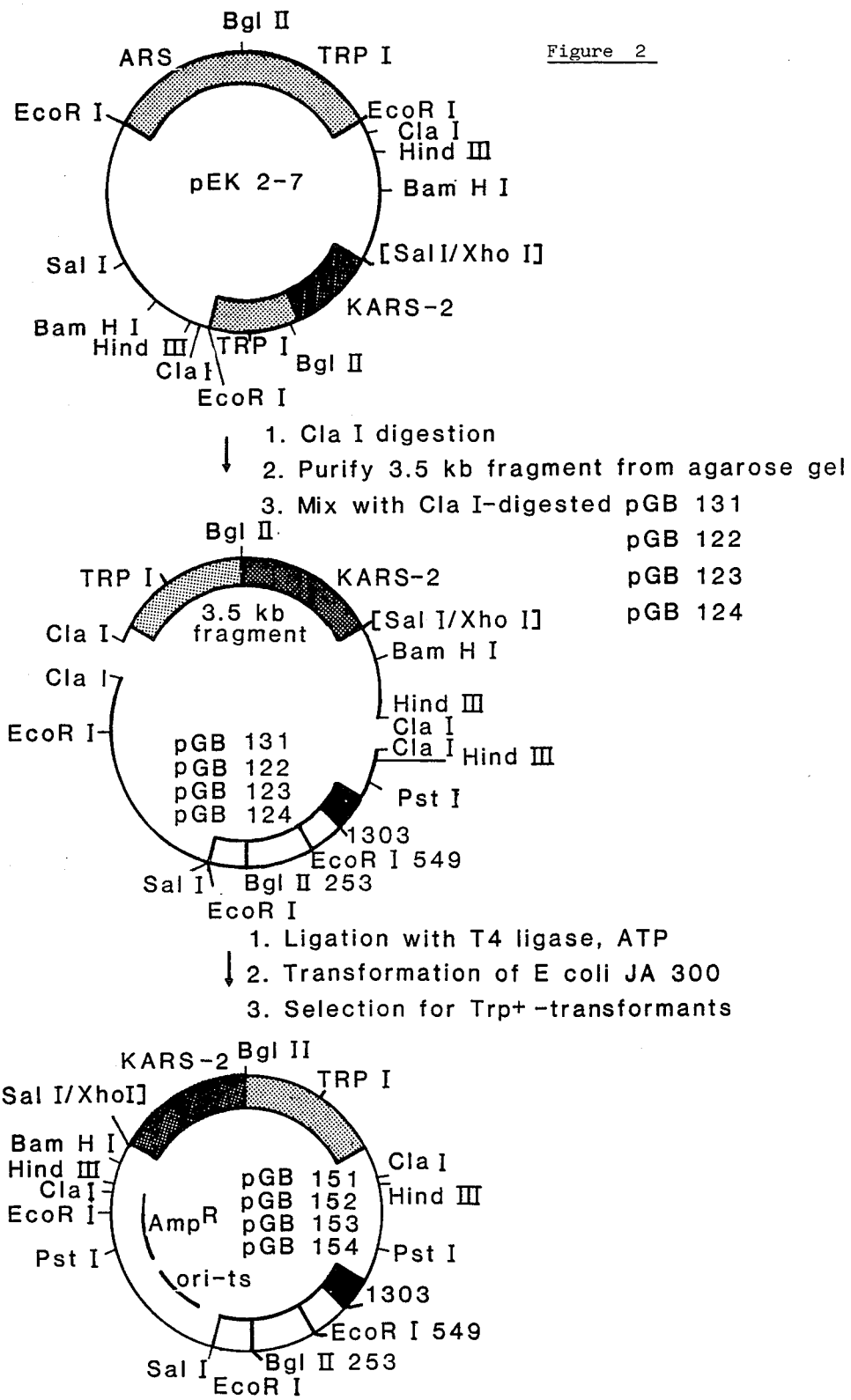
FIG. 2 is the pathway by which plasmids pGB151, pGB152, pGB153 and pGB154 are constructed from plasmids pGB131, pGB122, pGB123, and pGB124, respectively.

Autonomously replicating sequences derived from and replicating in Kluyveromyces were obtained as described in Examples 2 and 7-15. The autonomously replicating sequence in plasmid pKARS-2 is located on a 1.24 kb fragment and this fragment was cloned into the well-known plasmid YRp7 and a new plasmid pEK2-7 was obtained (FIG. 2). Digestion of pEK2-7 with endonuclease Cla I resulted in fragments of 3.5 and 5.5 kb, respectively. The 3.5 kb fragment containing the TRP1 gene derived from *S. cerevisiae* and the KARS-2 sequence derived from *K. lactis* (FIG. 2) was isolated from an agarose gel by electroelution and ligated to Cla I-digested plasmids pGB131, pGB122, and pGB123 and pGB124, respectively. The resulting mixture was transformed into *E. coli* JA300 (trpC) and characterization of plasmid DNA extracted from Trp+ transformants confirmed the construction of plasmids pGB151, pGB152, pGB153 and pGB154, respectively (FIG. 2).

C. Introduction of various promoter sequences in the plasmids directing the synthesis of the various maturation forms of preprochymosin.

The Sal I-digested plasmids containing the KARS-2 sequence, the TRP1 gene and the structural gene of preprochymosin or its various maturation forms are well suited to accept Sal I-linked promoter sequences to direct the synthesis of the distal structural gene in *K. lactis* transformants. In most cases the promoter sequences have to be provided with Sal I linkers. Any promoter sequence can be provided with such a Sal I linker and in the following Examples this is illustrated with 1. the isocytochrome cl promoter from *S. cerevisiae*
2. The lactose promoter from *K. lactis*

Figure 3:
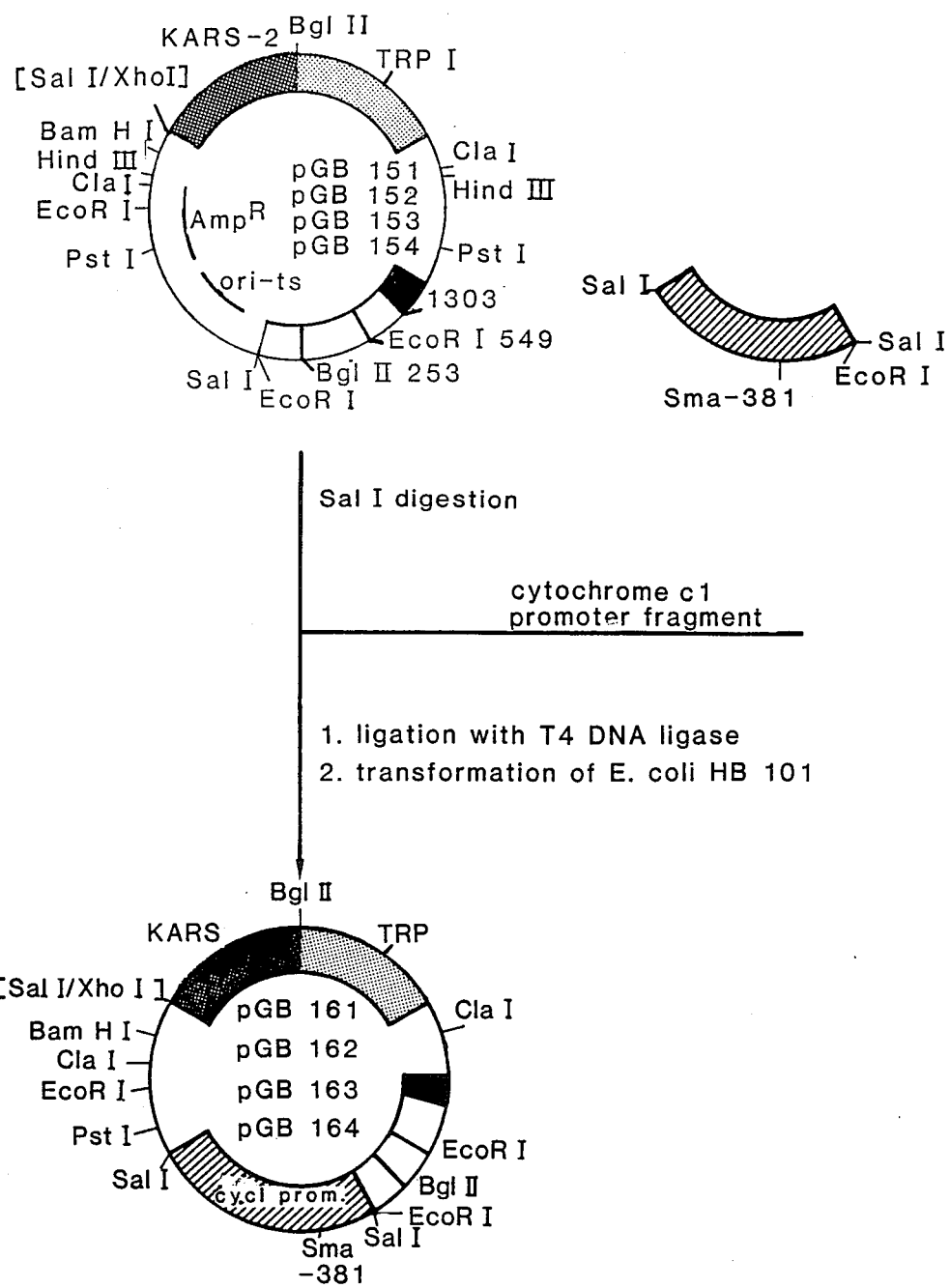
FIG. 3 is the pathway by which plasmids pGB161, pGB162, pGB163 and pGB164 are constructed from plasmids pGB151, pGB152, pGB153, and pGB154, respectively.

C1. Addition of Sal I linkers to the isocytochrome cl promotor from *S. cerevisiae* and introduction into plasmids. (FIG. 3)

Plasmid pYeCYCl consisting of the isocytochrome cl gene cloned into plasmid pBR322 was used as the starting material (G. Faye et al., Proc. Natl. Acad. Sci. USA 78 (1981) 2258).

From nucleotide sequence data it is known that an Eco RI site is present in the isocytochrome cl gene at nucleotide +8 (Ibid.)

Plasmid pYeCYCl was cleaved with endonuclease Eco Rl, ligated with T4 DNA ligase and transformed into *E. coli* HB101, yielding a plasmid pC15 containing the 1930 bp fragment carrying the promotor and 8 nucleotides of the isocytochrome cl gene.

Plasmid pC15 was cleaved with endonuclease Eco RI and incubated with nuclease Bal 31 for a short while to remove just a few nucleotides.

The Bal 31 digested ends were converted tô bluntends with DNA polymerase (Klenow fragment) and a phosphorylated Eco RI linker was ligated to this DNA. After incubation with endonuclease Eco RI, ligation and transformation into *E. coli*, a transformant pC15–R12 was identified in which 12 nucleotides from the cytochrome cl gene had been removed. A Sal I linker was introduced by cleaving plasmid pC15–R12 with endonuclease Eco RI, filling in the cohesive ends with DNA polymerase, ligation of a phosphorylated Sal I linker, incubation with endonuclease Sal I and recloning the resulting 1070 bp fragment in the Sal I digested plasmids pGB151, pGB152, pGB153 and pGB154, respectively, yielding the isocytochrome cl promotor containing plasmids pGB161, pGB162, pGB163 and pGB164, respectively as identified by colony hybridization with the $^{32}$P-labeled 1070 bp fragment as probe. Plasmid DNA was prepared from the positive clones and the correct orientation of the isocytochrome cl promotor was confirmed by the presence of a 850 bp fragment after digestion with endonuclease Sma I.

C2. Addition of Sal I linkers to the lactase promotor from *Kluyveromyces lactis* and introduction into plasmids.

The starting material was plasmid pK16 containing the lactase gene from *K. lactis* cloned into the Eco RI site of plasmid pBR322 (R. C. Dickson and J. S. Markin, Cell 15 (1978), 123).

Sequencing of large parts of the lactase structural gene and its promotor established the presence of a Cla I site at about 450 bp in the lactase structural gene. Plasmid pk16 was digested with endonuclease Cla I and the fragment containing the promoter and about 450 bp of the structural gene were recloned into the plasmid pBR322 digested with endonucleases Cla I and Acc I (partially). In one plasmid, pGB 182, the retained Cla I site at about 450 bp in the lactase structural gene was opened by incubation with endonuclease Cla I and trimmed by incubation with nuclease Bal 31. The Bal 31 ends were rendered blunt-ends by incubation with DNA polymerase and a phosphorylated Eco RI linker was ligated to this trimmed fragment. Digestion with endonuclease Eco RI and recloning of the trimmed fragment resulted in plasmid pGB 183, that had retained the lactase promotor and was devoid of the structural gene.

Sal I linkers were added to this fragment as described earlier in this example (16.C1). The Sal I linked lactase promotor was ligated to Sal I-cleaved plasmids pGB 151, pGB 152, pGB 153 and pGB 154, respectively, yielding plasmids pGB 171, pGB 172, pGB 173 and pGB 174, respectively.

Plasmids obtained as described in this Example 16 were introduced into *Kluyveromyces lactis* SD11 lac4 trpl by the Li+ method as described in Example 14, selecting for Trp+ transformants.

The presence of preprochymosin or its maturation forms in Kluyveromyces extracts was demonstrated by immunological ELISA techniques and by spotting aliquots of the extracts on nitrocellulose filters and assaying the filters as described by D. J. Kemp and A. F. Cowman (Proc. Natl. Acad. Sci. USA 78 (1981) 4520–4524).

Cell-extracts were prepared as follows: *K. lactis* transformants were grown at 30° C. for about 16-24 hours in YNB-medium containing 2% dextrose. Cells were harvested at OD$_{610}$ nm between 2.2 and 6.0 by centrifugation 6000 rpm for 10 minutes in a Sorvall G-S3 rotor. The pellet was resuspended in sterile distilled water to OD$_{600}$ of 600 and chilled on ice.

0.5 ml of this cell suspension was diluted with 0.5 ml of ice-cold water and mixed with 2 g of Ballotini beads (diameter 0.25-0.35 mm Braun-Melsungen GMBH, GFR).

The cells were disrupted by shaking for 4 minutes on a Vortex shaker at maximal speed. More than 95% of the cells were disrupted as checked by phase contrast microscopy. Cell debris was removed by centrifugation for 1 minute in an Eppendorf centrifuge. Aliquots of the extracts were frozen in liquid nitrogen and stored at −80° C.

1–5 μl aliquots of the cell extracts were spotted on nitrocellulose membrane filters. The filters were dried, wetted with 192 mM glycine, 25 mM Tris, 20% ethanol (pH 8.3) and incubated for 60 minutes at 22° C. The filters were subsequently incubated with preincubation buffer (0.35M NaCl, 10 mM Tris-HCl (pH 7.6), 2% bovine serum albumin) for 30 minutes. The filters were washed three times for 5 minutes with a solution containing RIA-buffer (0.125M NaCl, 10 mM Tris-HCl, pH 7.6, 0.1 mM PMSF, 1% Triton X100, 0.5% sodium desoxycholate, 0.1% sodium dodecylsulfate and 0.3% gelatin). The filters were incubated overnight at 4° C. in 1 ml RIA buffer containing 10 μl of chymosin antiserum. Antiserum was removed by washing with RIA buffer (three times) and incubated with 1 μCi $^{125}$I-protein A in 1 ml of RIA-buffer for 60 minutes at 22° C.

$^{125}$I-protein A was removed by washing with RIA buffer (5 times).

The filters were dried and autoratiographed overnight.

The presence of preprochymosin or its maturation forms in *K. lactis* transformants was clearly observed.

The presence of chymosin activity in cell extracts from *K. lactis* transformants was determined by high performance liquid chromatography (HPLC) as described by A. C. M. Hooydonk and C. Olieman, Netherl. Milk Dairy 36 (1982), 153.

50 μl of enzyme solution or extract was added to 1 ml of a 10% solution of milkpowder (Difco) in 10 mM CaCl$_2$.

The solution was incubated for 15 minutes at 31° C.

The reaction was stopped by adding 2 ml of 12% trichloroacetic acid (TCA). Almost all proteins were precipitated by TCA except glycomacropeptide (GMP) that has been cleaved from k casein by chymosin action.

Denatured proteins are pelleted by centrifugation and 1 ml of the clear supernatant was neutralised with 0.4 ml of 1N NaOH.

The solution was centrifuged again and the amount of GMP produced was detected with HPLC monitoring the extinction at 214 nm.

Extracts from *K. lactis* transformants containing prochymosin were first incubated at pH 2 for 2 hours and subsequently neutralized before performing the chymosin activity test. Chymosin was only found after the pH 2 treatment.

EXAMPLE 17

Kluyveromyces SD11 lac4 trpl expressing preprothaumatin and its various maturation forms after being transformed with plasmid pURK 528-01 containing the structural gene encoding preprothaumatin, the KARS2 sequence from *K. lactis*, the glyceraldehyde-3-phosphate dehydrogenase promoter from *S. cerevisiae* and the TRP1 gene from *S. cerevisiae*

This Example comprises a number of steps the most essential of which are:

1. Isolation of clones containing the glyceraldehyde-3-phosphate dehydrogenase (GAPDH) operon of *S. cerivisiae*

A DNA pool of the yeast *S. cerevisiae* was prepared in the hybrid *E. coli*-yeast plasmid PFL1 (M. R. Chevallier et al., Gene 11 (1980) 11–19) by a method similar to the one described by M. Carlson and D. Botstein, Cell 28

(1982) 145–154. Purified yeast DNA was partially digested with restriction endonuclease Sau 3A and the resulting DNA fragments (with an average length of 5 kb) were ligated by T4 DNA ligase in the dephosphorylated Bam HI site of pFL 1. After transformation of CaCl$_2$-treated *E. coli* cells with the ligated material a pool of about 30,000 ampicillin resistant clones was obtained. These clones were screened by a colony hybridization procedure (R. E. Thayer, Anal. Biochem., 98 (1979) 60–63) with a chemically synthesized and $^{32}$P-labeled oligomer with the sequence 5'TACCAG-GAGACCAACTT3'.

According to data published by J. P. Holland and M. J. Holland (J. Biol. Chem., 255 (1980) 2596–2605) this oligomer iscomplementary with the DNA sequence encoding amino acids 306–310 (the wobble base of the last amino acid was omitted from the oligomer) of the GAPDH gene. Using hybridization conditions described by R. B. Wallace et al., Nucleic Acid Res., 9 (1981) 879–894, six positive transformants could be identified. One of these harboured a plasmid which was named PFL 1-33. The latter plasmid contained the GAPDH gene including its promotor/regulation region and its transcription termination/polyadenylation region. The approximately 9 kb long insert of pFL 1-33 has been characterized by restriction enzyme analysis (FIG. 4) and partial nucleotide sequence analysis (FIGS. 5 and 6).

2. Isolation of the GAPDH promotor/regulation region and its introduction into a preprothaumatin-encoding plasmid On the basis of the restriction enzyme analysis and the nucleotide sequence data of the insert of plasmid pFL 1-33, the DNA initiation/regulation region of the GAPDH gene was isolated as an 800 nucleotides long Dde I fragment. To identify this promoter fragment, plasmid pFL 1-33 was digested with Sal I and the three resulting DNA fragments were subjected to a Southern blot hybridization test with the chemically synthesized oligomer (E. M. Southern, J. Mol. Biol. 98 (1975) 503–517).

Figure 4:
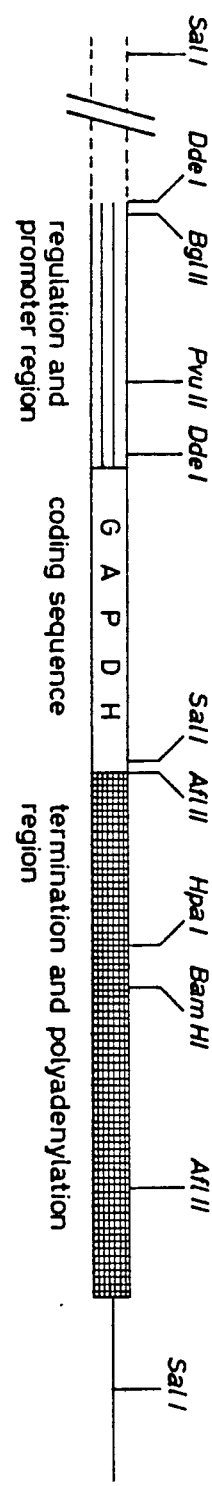
FIG. 4 is a restriction map of the insert of plasmid pF1 1-33. A schematic diagram of the GAPDH gene is correlated with the restriction map.

A positively hybridizing 4.3 kb long restriction fragment was isolated on a preparative scale by electroelution from a 0.7% agarose gel and was then cleaved with Dde I. Of the resulting Dde I fragments only the largest one had a recognition site for Pvu II, a cleavage site located within the GADPH regulon region (FIG. 4). The largest Dde I fragment was isolated and incubated with Klenow DNA polymerase and four dNTP's (A. R. Davis et al., Gene 10 (1980) 205–218) to generate a blunt-ended DNA molecule. After extraction of the reaction mixture with phenol/chloroform (50/50 v/v), passage of the aqueous layer through a Sephadex G50 column and ethanol precipitation of the material present in the void volume, the DNA fragment was equipped with the $^{32}$P-labeled Eco RI linker 5'GGAATTCC3' by incubation with T4 DNA ligase. Due to the Klenow polymerase reaction and the subsequent ligation of the Eco RI linker, the original Dde I sites were reconstructed at the end of the regulon fragment. To inactivate the ligase the reaction mixture was heated to 65° C. for 10 minutes, then sodium chloride was added (final concentration 50 mmol/l) and the whole mix was incubated with Eco RI. Incubation was terminated by extraction with phenol/chloroform, the DNA was precipitated twice with ethanol, resuspended and then ligated into a suitable vector molecule. Since the Dde I regulon fragment was equipped with Eco RI sites it can be easily introduced into the Eco RI site of pUR 528 (L. Edens et al., Gene 18 (1982) 1–12 to create a plasmid in which the yeast regulon is adjacent to the structural gene encoding preprothaumatin. The latter plasmid was obtained by cleavage of pUR 528 with Eco RI, treatment of the linearized plasmid molecule with (calf intestinal) phosphatase to prevent self-ligation and incubation of each of these vector molecules as well as the purified Dde I promotor fragment with T4 DNA ligase. Transformation of the various ligation mixes in CaCl$_2$-treated *E. coli* HB101 cells yielded several ampicillin resistant colonies. From some of these colonies plasmid DNA was isolated (H. C. Birnboim and J. Doly, Nucleic Acids Res. 7 (1979) 1513–1523) and incubated with PvuII to test the orientation of the insert.

In the nomenclature plasmids containing the Eco RI (Dde I) GAPDH regulon fragment in the correct orientation (i.e. transcription from the GAPDH regulon occurs in the direction of a downstream located structural gene) are indicated by the addendum-01 to the original code of the plasmid (for example pUR 528 is changed into pUR 528-01; see FIG. 7).

To facilitate manipulation of plasmids containing the Eco RI regulon fragment, one of the two Eco RI sites was destroyed. Two μg of plasmid DNA (e.g. pUR 528-01) was partially digested with Eco RI and then incubated with 5 units Mung bean nuclease (obtained from P.L. Biochemicals Inc.) in a total volume of 200 μl in the presence of 0.05 moles/l sodium acetate (pH 5.0), 0.05 moles/l sodium chloride and 0.001 moles/l zinc chloride for 30 minutes at room temperature to remove sticky ends. The nuclease was inactivated by addition of SDS to a final concentration of 0.1% (D. Kowalski et al., Biochemistry 15 (1976) 4457–4463) and the DNA was precipitated by the addition of 2 volumes of ethanol. Linearized DNA molecules were then religated by incubation with T4 DNA ligase and used to transform CaCl$_2$-treated *E. coli* cells. Plasmid DNA isolated from ampicillin resistant colonies was tested by cleavage with Eco RI and Mlu I for the presence of a single Eco RI site adjacent to the thaumatin gene (cf. FIG. 7).

Plasmids containing the GAPDH promotor fragment but having only a single Eco RI recognition site adjacent to the ATG initiation codon of a downstream located structural gene are referred to as −02 type plasmids (for example: pUR 528-01 is changed into pUR 528-02; see FIG. 7).

3. Reconstitution of the original GAPDH promotor/regulation region in plasmids encoding preprothaumatin by introduction of a synthetic DNA fragment (FIG. 8)

As shown by the nucleotide sequence depicted in FIG. 5, the Eco RI (Dde I) GAPDH promotor fragment contains the nucleotides −850 to −39 of the original GAPDH promoter/regulation region. Not contained in this promoter fragment are the 38 nucleotides preceding the ATG initiation codon of the GAPDH encoding gene. The latter 38-nucleotides long fragment contains the PuCACACA sequence, which is found in several yeast genes. Said PuCACACA sequence situated about 20 bp upstream of the translation start site (M. J. Dobson et al., Nucleic Acid Res., 10 (1982) 2625–2637) provides the nucleotide sequence upstream of the ATG codon which is optimal for protein initiation (M. Kozak, Nucleic Acids Res. 9 (1981) 5233–5252). Moreover, these nucleotides allow the formation of a small loop structure which might be involved in the regulation of expression of the GAPDH gene. On the basis of the above-mentioned arguments, introduction of the 38 nucleotides in between the Dde I promotor-fragment and the ATG codon of a downstream located structural gene was considered necessary to improve promotor activity as well as translation initiation.

As outlined in FIG. 9 the missing DNA fragment was obtained by the chemical synthesis of two partially overlapping oligomers. The Sac I site present in the overlapping part of the two oligonucleotides was introduced for two reasons: (i) to enable manipulation of the nucleotide sequence immediately upstream of the ATG codon including the construction of poly A-tailed yeast expression vectors; (ii) to give a cleavage site for an enzyme generating 3'-protruding ends that can easily and reproducibly be removed by incubation with T4 DNA polymerase in the presence of the four dNTP's. Equimolar amounts of the two purified oligomers were phosphorylated at their 5'-termini, hybridized (J. J. Rossi et al., J. Biol. Chem. 257 (1982) 9226-9229) and converted into a double-stranded DNA molecule by incubation with Klenow DNA polymerase and the four dNTP's under conditions which have been desribed for double-stranded DNA synthesis (A. R. Davis et al., Gene 10 (1980) 205-218). Analysis of the reaction products by electrophoresis through a 13% acrylamide gel followed by autoradiography showed that more than 80% of the starting single-stranded oligonucleotides were converted into double-stranded material. The DNA was isolated by passage of the reaction mix over a Sephadex G50 column and ethanol precipitation of the material present in the void volume. The DNA was then phosphorylated by incubation with polynucleotide kinase and digested with Dde I. To remove the nucleotides cleaved off in the latter reaction, the reaction mix was subjected to two precipitations with ethanol.

Figure 8:
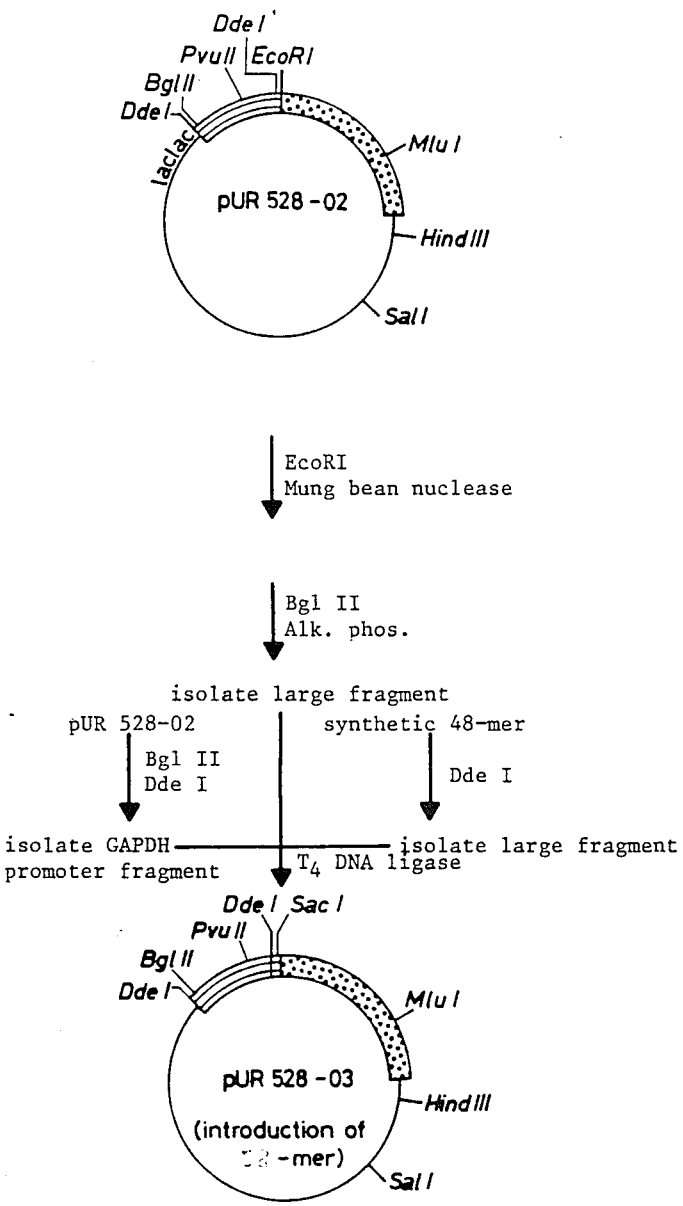
FIG. 8 is the pathway by which plasmid pUR 528-03 is constructed from pUR 528-02.

As shown in FIG. 8 cloning of the resulting synthetic DNA fragment was carried out by the simultaneous ligation of this fragment and a BglII-DdeI GAPDH promoter regulation fragment in a vector molecule from which the Eco RI site preceding the ATG initiation codon was removed by Mung bean nuclease digestion (cf. step 2). The BglII-DdeI promoter/regulation fragment was obtained by digestion of plasmid pUR 528-02 with DdeI and BglII. Separation of the resulting restriction fragments by electrophoresis through a 2% agarose gel and subsequent isolation of the fragment from the gel yielded the purified 793 nucleotides long promoter/regulation fragment. In the plasmid pUR 528-02 the nucleotide sequence preceding the ATG codon is 5'-GAATTC(T)ATG-3' (EP-PA 54330 and EP-A 54331), which is different from the favourable nucleotide sequence given by M. Kozak (Nucleic Acids Res. 9 (1981) 5233-5252). Since our aim was to reconstitute the original GAPDH promotor/regulation/protein initiation region as accurately as possible, the Eco RI site was removed in order to ligate the synthetic DNA fragment to the resulting blunt-end. Removal of the Eco RI site was accomplished by Mung bean nuclease digestion of Eco RI-cleaved pUR 528-02 DNA.

Subsequently the plasmid DNA was digested with BglII and incubated with phosphatase. After separation of the two DNA fragments by electrophoresis through a 0.7% agarose gel, the largest fragment was isolated and used as the vecotor in which the BglII-DdeI promoter fragment as well as the -DdeI-treated—synthetic DNA fragment were ligated. Plasmids in which the DdeI promoter/regulation fragment together with the Sac I recognition site-containing synthetic DNA fragment are introduced are indicated by the addendum −03 (for example: pUR 528-02 is changed into pUR 528-03).

Figure 10:
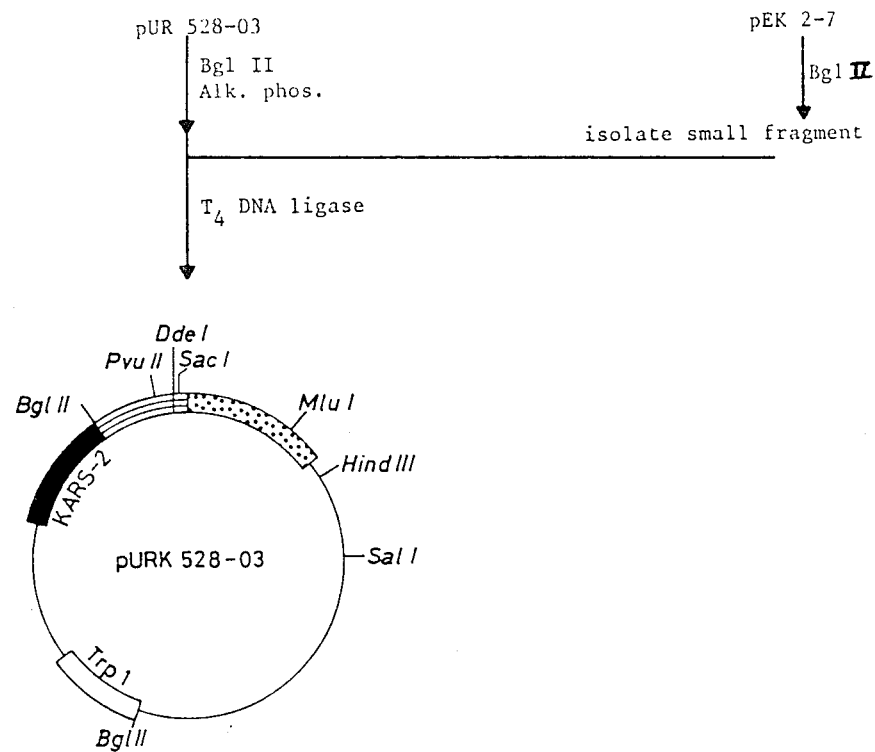
FIG. 10 is the pathway by which pURK 528-03 is constructed.

4. Introduction of the KARS2 replicon from *K. lactis* and the TRP1 gene from *S. cerevisiae* in preprothaumatin-encoding plasmids The KARS2 replicon and the TRP1 gene were excised from pEK 2-7 by digestion with Bgl II, followed by isolation from a 0.7% agarose gel of the 3.5 kb fragment. This purified fragment was inserted in the dephosphorylated Bgl II cleavage site of pUR 528-03 by incubation with T4 DNA ligase. Transformation of the ligation mix in *E. coli* yielded plasmid pURK 528-03 (FIG. 10). Transformants generated by the introduction of plasmid pURK 528-03 into *K. lactis* SD11 cells by the Li+ method were shown to synthesize thaumatin-like proteins assayed as described by L. Edens et al., Gene 18 (1982) 1-12, see FIG. 11.

A culture of *Kluyveromyces lactis* SD11 containing plasmid pURK 528-02 has been deposited with the Centraal Bureau voor Schimmelcultures, Baarn, the Netherlands and has been assigned the accession number CBS 8157.

We claim:

1. A transformed Kluyveromyces cell comprising a DNA sequence comprising a region encoding a polypeptide, heterologous to said cell, with said DNA sequence resulting from joining of at least two DNA molecules to provide a gene functional for expression in said Kluyveromyces cell, wherein said gene functional for expression comprises at least a promoter regulation region and a structural gene.

2. A Kluyveromyces expression vector comprising in the 5'-3' direction of transcription:
   (a) a promoter regulation region functional in Kluyveromyces;
   (b) a DNA sequence encoding a polypeptide heterologous to said Kluyveromyces under the regulation of said promoter regulation region;
   (c) a transcription terminator; and joined thereto
   (d) a selection marker; and
   (e) a KARS.

3. A process for preparing a new strain of Kluyveromyces yeast, which comprises:
   transforming Kluyveromyces yeast cells with a vector comprising:
   in the 5'-3' direction of transcription:
   (a) a promoter regulation region functional in Kluyveromyces;
   (b) a DNA sequence, encoding a polypeptide heterologous to said cells, under the regulation of said promoter regulation region;
   (c) a transcription terminator; and joined thereto
   (d) a selection marker; propagating the resultant transformed cells in a growth-sustaining medium.

4. A process according to claim 3, wherein at least (a), (b), (c) and (d) are integrated into the genome of said cells.

5. A process according to claim 3, wherein said vector comprises:
   (a) an origin of replication functional in Klyyveromyces.

6. A cell according to claim 1, wherein said polypeptide is chymosin, prochymosin, preprochymosin, or pseudochymosin.

7. A cell according to claim 1, wherein said polypeptide is β-galactosidase.

8. A cell according to claim 1, wherein said DNA sequence comprises at least one of a selection marker or a replication sequence for autonomous replication of said DNA sequence in said cell.

9. A cell according to claim 8, wherein said replication sequence is the 2 micron plasmid replication sequence.

10. A cell according to claim 8, wherein said replication sequence is a KARS sequence from Kluyveromyces.

11. A cell according to any of claims 1, 6, 7, 8, 9, or 10, wherein said gene is integrated into the genome of said cell.

12. A cell according to any of claims 1, 6, 7, wherein said DNA sequence comprises the plasmid pL4, PTY75-LAC4, pKARS2 or pKARS12.

13. *K. lactis* SD69 lac4 (PTY75-LAC4).

14. *K. lactis* SD11 lac4 trp1 (pKARS12).

15. *K. lactis* SD69 lac4 (pL4).

16. A Kluyveromyces expression vector according to claim 2, further comprising a sequence homologous with a Kluyveromyces genomic sequence.

17. A Kluyveromyces expression vector according to claim 2, wherein said origin of replication is the 2 micron origin of replication.

18. A Kluyveromyces expression vector according to claim 16, wherein said polypeptide is chymosin, prochymosin, preprochymosin, or pseudochymosin.

19. Plasmid pKARS12.

20. Plasmid pKARS2.

21. Plasmid pL4.

22. Plasmid PTY75-LAC4.

23. The process according to claim 3, wherein said cells are transformed as protoplasts.

24. The process according to claim 3, wherein said cells are transformed as whole cells.

25. The process according to claim 3, wherein said origin of replication is the Saccharomyces 2 micron plasmid origin of replication, *Saccharomyces ars* or a KARS.

26. The process according to claim 3, wherein said vector is pL4, pKARS12, or PTY75-LAC4.

27. The process according to claim 3, wherein said Kluyveromyces cells are *K. lactis*.

28. The process according to claim 3, wherein said Kluyveromyces cells are *K. fragilis*.

29. The process according to claim 3, wherein said transformed cells are incubated in a medium of about 0.6M KCl.

30. A process for preparing a polypeptide in Kluyveromyces which comprises:

* * * * *

UNITED STATES PATENT AND TRADEMARK OFFICE
CERTIFICATE OF CORRECTION

PATENT NO. : 4,859,596

DATED : August 22, 1989

INVENTOR(S) : Cornelis P. Hollenberg, et al.

It is certified that error appears in the above-identified patent and that said Letters Patent is hereby corrected as shown below:

```
Title page, item [56], line 10, delete "8202091 5/1982 European
                Pat. Off...".
Title page, item [73], change "MA Delft" to --2600 MA Delft--.
Column 3, line 26, change "kluyveromyces" to --Kluyveromyces--.
Column 3, line 46, change "pFl" to --pFL--.
Column 3, line 49, change "pFl" to --pFL--.
Column 3, line 51, change "pFl" to --pFL--.
Column 3, line 62, change "K. lactis" to --K. lactis--.
Column 4, line 22, change "that" to --than--.
Column 4, line 41, change "his" to --this--.
Column 7, line 52, change "32p-labelled" to --$^{32}$P-labelled--.
Column 7, line 53, change "baceterial" to --bacterial--.
Column 8, line 28, change "PTY75-LAC4)" to --(PTY75-LAC4)--.
Column 8, line 32, change "Hybride" to --Hybrid--.
Column 8, line 65, change "optical" to --optimal--.
Column 9, line 26, change "ws" to --was--.
Column 9, line 27, change "gal K2xyl-5" to --galK2 xyl-5--.
Column 9, line 28, change "supE44-$\lambda$-lac" to --supE44-$\lambda$-lac--.
Column 9, line 32, change "formationof" to --formation of--.
Column 11, line 23, change "frequence" to --frequency--.
Column 11, line 32, change "Table for" to --Table.  For--.
Column 11, line 34, change "example" to --Examples--.
```

UNITED STATES PATENT AND TRADEMARK OFFICE
CERTIFICATE OF CORRECTION

PATENT NO. : 4,859,596                                Page 2 of 2

DATED      : August 22, 1989

INVENTOR(S): Cornelis P. Hollenberg, et al.

It is certified that error appears in the above-identified patent and that said Letters Patent is hereby corrected as shown below:

```
Column 11, line 34, after "4" insert --and 5--.
Column 13, line 30, change "ethidiumbromide" to
                    --ethidium bromide--.
Column 13, line 33, change "were" to --was--.
Column 14, line 20, change "was" to --were--.
Column 15, line 23, change "pkl6" to --PKL6--.
Column 15, line 59, after "tion" insert --at--.
Column 16, line 40, change "are" to --were--.
Column 16, line 66, change "PFL1" to --pFL1--.
Column 17, line 5, change "pFL 1" to --pFL1--.
Column 19, line 51, change "EP-PA" to --EP-A--.
Column 19, line 65, change "vecotor" to --vector--.
Claim 3, line 12, change "propagating the resultant" to
                    --and--.
Claim 3, line 13, change "transformed" to
                    --propagating the resultant--.
Claim 5, line 3, change "Klyyvero" to --Kluyvero--.
Claim 30, after line 2, insert --cultivating Kluyveromyces
                    cells according to any one of Claims 1 or
                    6 to 10 or 13 to 15--.
```

Signed and Sealed this

Sixteenth Day of July, 1991

Attest:

HARRY F. MANBECK, JR.

*Attesting Officer*       *Commissioner of Patents and Trademarks*